(12) United States Patent
Kermani et al.

(10) Patent No.: US 7,702,466 B1
(45) Date of Patent: Apr. 20, 2010

(54) SYSTEMS AND METHODS FOR SELECTION OF NUCLEIC ACID SEQUENCE PROBES

(75) Inventors: Bahram Ghaffarzadeh Kermani, San Diego, CA (US); Timothy K. McDaniel, San Diego, CA (US); Shawn C. Baker, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 1156 days.

(21) Appl. No.: 10/881,021

(22) Filed: Jun. 29, 2004

(51) Int. Cl.
*G01N 33/48* (2006.01)

(52) U.S. Cl. ..................................................... 702/19
(58) Field of Classification Search ..................... 702/19
See application file for complete search history.

(56) References Cited

U.S. PATENT DOCUMENTS

| | | |
|---|---|---|
| 5,429,807 A | 7/1995 | Matson et al. |
| 5,436,327 A | 7/1995 | Southern et al. |
| 5,561,071 A | 10/1996 | Hollenberg et al. |
| 5,583,211 A | 12/1996 | Coassin et al. |
| 5,658,734 A | 8/1997 | Brock et al. |
| 5,837,858 A | 11/1998 | Brennan |
| 5,874,219 A | 2/1999 | Rava et al. |
| 5,919,523 A | 7/1999 | Sundberg et al. |
| 6,023,540 A | 2/2000 | Walt et al. |
| 6,136,269 A | 10/2000 | Winkler et al. |
| 6,200,737 B1 | 3/2001 | Walt et al. |
| 6,251,588 B1 | 6/2001 | Shannon et al. |
| 6,287,768 B1 | 9/2001 | Chenchil et al. |
| 6,287,776 B1 | 9/2001 | Hefti |
| 6,288,220 B1 | 9/2001 | Kambara et al. |
| 6,291,193 B1 | 9/2001 | Khodadoust |
| 6,297,006 B1 | 10/2001 | Drmanac et al. |
| 6,327,410 B1 | 12/2001 | Walt et al. |
| 6,346,413 B1 | 2/2002 | Fodor et al. |
| 6,355,431 B1 | 3/2002 | Chee et al. |
| 6,416,949 B1 | 7/2002 | Dower et al. |
| 6,421,668 B1 | 7/2002 | Yakhini et al. |
| 6,429,027 B1 | 8/2002 | Chee et al. |
| 6,514,751 B2 | 2/2003 | Johann et al. |
| 6,524,793 B1 | 2/2003 | Chandler et al. |
| 6,610,482 B1 | 8/2003 | Fodor et al. |
| 2002/0102578 A1 | 8/2002 | Dickinson et al. |

FOREIGN PATENT DOCUMENTS

| | | |
|---|---|---|
| EP | 742 287 | 11/1996 |
| EP | 799 897 | 10/1997 |
| WO | WO 93/17126 | 9/1993 |
| WO | WO 95/11995 | 5/1995 |
| WO | WO 95/35505 | 12/1995 |
| WO | WO 98/40726 | 9/1998 |
| WO | WO 98/50782 | 11/1998 |
| WO | WO 98/59066 | 12/1998 |
| WO | WO 00/63437 | 10/2000 |

OTHER PUBLICATIONS

Tobler et al. "Evaluating Machine Learning Approaches for Aiding Probe Selection for Gene-Expression Arrays," Bioinformatics (2002) vol. 17, Suppl. 1, pp. S164-S171.*
Demirkaya et al. "Segmentation of Microarray cDNA Spots Using MRF-based Method," Proceeding of the $25^{th}$ Annual Conference of the IEEE EMBS (2003) vol. 1, pp. 674-677.*
Chen et al. "Ratio Statistics of Gene Expression Levels and Applications to Microarray Data Analysis," Bioinformatics (2002) vol. 18, No. 9, pp. 1207-1215.*
Shi et al., "Comparison of Human Dental Pulp and Bone Marrow Stromal Stem Cells by cDNA Microarray Analysis," Bone (2001) vol. 29, No. 6, pp. 532-539.*
Chiang et al. "Single-Cell Transcript Analysis of Pancreas Development," Developmental Cell, (Mar. 2003) vol. 4, pp. 383-393.*
Heller et al. "Discovery and Analysis of Inflammatory Disease-Related Genes using cDNA Microarrays," Proc. Natl. Acad. Sci. (1997) vol. 94, pp. 2150-2155.*
Kang et al. "Identification of Genes with Differential Expression in Acquired Drug-Resistant Gastric Cancer Cells using High-Density Oligonucleotide Microarrays," Clinical Cancer Research (Jan. 2004) vol. 10, pp. 272-284.*
Collins et al., Experimental selection and performance of 60-mer oligonucleotide probes for profiling global gene expression. Agilent Technologies. Publication No. 598-9189EN, May 2003.
Lowe and Tipping, NeuroScale: Novel topographic feature extraction using RBF networks. Neural Computing Research Group, Aston University, http://www.ncrg.aston.ac.uk, (1997).
Nabney, Searching for patterns in activity across multiple targets project description. Neural Computing Research Group, Department of Computer Science and Applied Mathematics, Aston University, (1997).

\* cited by examiner

*Primary Examiner*—Jerry Lin
(74) *Attorney, Agent, or Firm*—McDermott Will & Emery

(57) ABSTRACT

Probe selection techniques are based, at least in part, on empirical evidence concerning the hybridization of candidate probes across a panel of diverse biological isolates. Various principles concerning the behavior of the most preferable probes across a panel of diverse biological isolates are applied to select from among a set of candidate probes or to eliminate candidate probes from further consideration.

32 Claims, 5 Drawing Sheets

SYSTEMS AND METHODS FOR SELECTION OF NUCLEIC ACID SEQUENCE PROBES

BACKGROUND

1. Field of the Invention

Embodiments of the invention relate to probes for detecting nucleic acid sequences, and particularly to the selection of probes from among a set of candidate probes.

2. Related Technology

The basic principles of molecular biology are well known. The DNA molecule is composed of complementary strings of nucleotide bases. Sequences of bases within the DNA molecule referred to as genes represent the amino acid sequences of individual proteins. To form a protein, the DNA molecule is transcribed to create an RNA molecule having a nucleic acid sequence that is complementary to the sequence of the gene for that protein. The RNA molecule is transported to a ribosome where the protein is constructed based on the information represented by the nucleic acid sequence of the RNA.

A current goal of genetic research is to identify relationships between biological conditions and specific genes in the genome. One method for identifying these relationships is to detect the RNA molecules that are present in specific tissues and to search for correlations between the presence of a particular RNA molecule and known conditions of the tissues in which it is found. The detection of nucleic acid sequences such as genes and RNA molecules may be performed using nucleic acid probes. A probe is typically a molecule that includes a nucleic acid sequence that is complementary to a nucleic acid sequence within a target molecule of interest, such as a gene or an RNA molecule. The probe can also include a marker that produces a signal which can be detected to determine whether the probe has hybridized to another nucleic acid sequence. Alternatively, the target nucleic acid can be labeled for detection of a hybrid between probe and target.

Nucleic acid probes are widely used in nucleic acid array detection systems. In these systems, an array of discrete locations is formed on a substrate. Each discrete location is composed of a large number of identical probe molecules (e.g., 100,000 probes). An exemplary array is a bead array in which discrete locations include attached beads each bearing a unique probe type. A bead array typically includes multiple beads having the same probe, and may also include other beads containing other probes. The array is exposed to a sample (e.g., a labeled RNA derived from a tissue sample) in a hybridization chamber for a period of time to allow hybridization to occur between the probes and target nucleic acid sequences in the sample. A scanner is then used to create data representing the signal detected from probes that have hybridized to targets in the sample, and image processing is performed to determine a signal value for the probe as a whole. Typically the signal is a fluorescent signal that is detected by an optical scanner. High fluorescence indicates that the probe underwent significant hybridization to nucleic acid sequences in the tissue, suggesting a high presence of the target sequence in the tissue. Low fluorescence indicates that very little hybridization occurred, indicating very little presence of the target sequence in the tissue.

A problem of nucleic acid probes is that it is possible for a probe to hybridize to nucleic acid sequences that are not a perfect complement of the probe sequence but that have sufficient similarity to enable hybridization to occur, resulting in the generation of a signal even though the target sequence is not present. Furthermore, hybridization can be confounded by the fact that genes can contain multiple splice isoforms. If a probe is designed for a sequence that is found in multiple splice isoforms, it will not specifically detect the targeted isoform. Because the public sequence databases do not contain all splice isoforms of all genes documented, a probe designed based on the current state of information can still be non-specific due to hybridization to these undocumented variants.

Bioinformatic techniques may be used to improve probe selection by simulating the hybridization of candidate probes to nucleic acid sequences other than that of their target. For example, consider a human gene comprised of a sequence of 10,000 bases. Using informatic techniques, every unique nucleic acid sequence of a given length (e.g., 70 bases) of the gene may be defined as a candidate probe, and the hybridization potential of each candidate probe may then be simulated at every known unique location along the entire length of the human genome. The results of these simulations allow candidates having the highest theoretical selectivity for the target gene to be identified.

While informatic methods improve probe selection, experience has shown that probes selected in this manner often do not perform as expected, in that they do not hybridize to the target as efficiently as expected, or show greater than expected hybridization to non-target sequences. Thus there continues to be a need for techniques that can improve the probe selection process.

SUMMARY

Embodiments of the invention provide probe selection techniques that are based, at least in part, on empirical evidence concerning the hybridization of candidate probes across a panel of nucleic acids from diverse biological isolates. In accordance with embodiments of the invention, various principles concerning the behavior of the most preferable probes across a panel of diverse biological isolates are used to select from among a set of candidate probes or to eliminate candidate probes from further consideration.

In accordance with one embodiment, a dimensional reduction process is performed on candidate probe intensity pattern data to identify groups of probes having highly similar intensity patterns. This may be implemented as a method that comprises processing intensity pattern data for a set of candidate probes, identifying a most represented group among the one dimensional values, and designating candidate probes corresponding to the most represented group as selected probes. The intensity pattern data may represent intensities of markers associated with the candidate probes upon hybridization to nucleic acid sequences of each of a set of diverse biological isolates, and the processing may generate a one dimensional value corresponding to each candidate probe, with the relative similarities between the one dimensional values representing the relative similarities of their corresponding intensity patterns;

In accordance with another embodiment, probes are hybridized to samples of diverse biological isolates and to samples comprised of known mixtures of those diverse biological isolates to identify probes that exhibit unexpected hybridization behavior in the presence of the biological isolate mixtures. This may be implemented as a method that comprises storing intensity pattern data for a set of candidate probes, calculating expected intensities for each of the candidate probes for the one or more mixtures based on said predetermined amounts and actual intensities of the candidate probe corresponding to the constituent biological isolates of the mixtures; and eliminating candidate probes based on comparison of the actual intensities of the probes for said nucleic acid sequences of the mixtures and the expected intensities of the probes for the nucleic acid sequences of the mixtures. The intensity pattern data may represent intensities of markers associated with the probes upon hybridization to nucleic acid sequences of each of a set of diverse biological isolates, and intensities of markers associated with the probes upon hybridization to target nucleic acid sequences of one or more mixtures in predetermined amounts of selected ones of the diverse biological isolates.

In accordance with another embodiment, probes are hybridized to biological isolates of an organism having a genome that is essentially orthogonal to the genome of the organism of interest to identify probes exhibiting significant hybridization to the nucleic acids of the orthogonal organism. This may be embodied as a comprising obtaining intensity pattern data for a set of candidate probes, and eliminating any candidate probe having an intensity value for a biological isolate of an organism having the orthogonal genome that exceeds a threshold value. The intensity pattern data may represent intensities of markers associated with said probes upon hybridization to nucleic acids of each of a set of diverse biological isolates, and the set of diverse biological isolates may comprise one or more biological isolates from at least one organism of interest, and biological isolates from one or more organisms having a genome that is essentially orthogonal to the genome of the at least one organism of interest.

In accordance with another embodiment, probes are hybridized to a panel of diverse biological isolates and candidate probes are selected or eliminated based on the dynamic range of their hybridization to the diverse biological isolates. This may be implemented as a method comprising storing intensity pattern data for a set of candidate probes, wherein the intensity pattern data represents intensities of markers associated with the candidate probes upon hybridization to nucleic acid sequences of each of a set of diverse types of biological isolates, evaluating a parameter for each candidate probe that is representative of the dynamic response of the candidate probe across the diverse biological isolates, and designating one or more candidate probes as selected probes based on the evaluations of the parameter.

In accordance with another embodiment, probes are hybridized to a panel of diverse biological isolates, multiple parameters are evaluated for each probe, and probes are selected or eliminated based on a weighted combination of the evaluated parameters. This may be implemented as a method comprising storing intensity pattern data for a set of candidate probes, wherein the intensity pattern data represents intensities of markers associated with the probes upon hybridization to nucleic acid sequences of each of a set of diverse biological isolates, evaluating a plurality of parameters for each candidate probe using its corresponding intensity pattern data, each parameter being indicative of the desirability of the respective candidate probe, generating a score for each candidate probe based on a weighted combination of the evaluations of said parameters for the probe, and eliminating one or more of the candidate probes based on its score.

In accordance with another embodiment, a dimensional reduction process is performed to identify one or more groups of similar candidate probes, and processing in accordance with various combinations of the aforementioned embodiments is performed to select or eliminate candidate probes from those groups.

DETAILED DESCRIPTION

Described herein are various processes that may be used in selecting nucleic acid sequence probes from among a set of candidate probes. These processes utilize computational techniques that operate on empirical data representing the hybridization behavior of the candidate probes in the presence of nucleic acids from various diverse biological isolates. These computational techniques are preferably implemented in a programmable computing device that includes one or more microprocessors, random access memory for providing a working memory space, communication interfaces for exchanging data or signals with various external systems and devices, and programming code for controlling the computing device to perform processing as described herein. Embodiments of the inventions described herein include these processes, the programmable devices that are configured to perform these processes, and computer readable media storing programming code for controlling a programmable device to perform these processes. The following descriptions of embodiments specify functions to be performed, the input data on which the functions are performed, and the intermediate and output data produced as a result of those functions. Those having ordinary skill in the art are capable of implementing the various embodiments of the invention and alternatives to those embodiments based on these descriptions.

Figure 1:
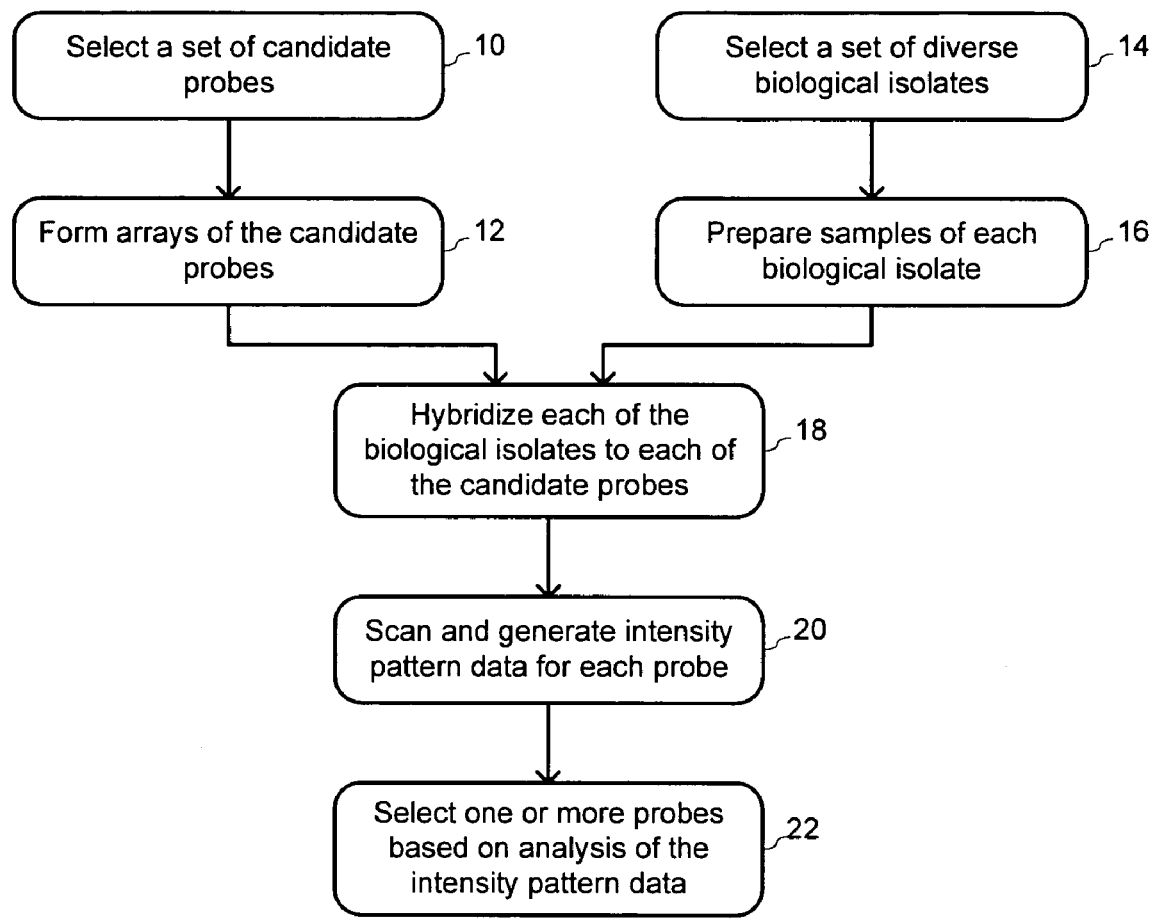
FIG. 1 shows a high level process flow in which embodiments of the invention may be implemented.

A process flow in which various embodiments of the invention may be utilized is shown in FIG. 1. The process flow of FIG. 1 is a high-level description of a process for selecting probes for a target nucleic acid sequence. Initially a set of candidate probes for a target nucleic acid sequence is selected (10). The candidate probes may be selected using informatic techniques such as those described herein to identify nucleic acid sequences having a high theoretical likelihood of highly selective hybridization to the target sequence. Arrays of the candidate probes are then formed (12). Each array is typically comprised of multiple beads for one or more probes, the beads being joined to a substrate, and each bead containing probe molecules comprised of a nucleic acid sequence and a marker. Those skilled in the art will recognize that other array platforms can be used, such as those set forth below in further detail.

A set of diverse biological isolates is selected for use in the methods (14), and one or more samples of each biological isolate is prepared (16). Examples of diverse biological isolates include, but are not limited to, biological isolates derived from different cell types, different cell lines, cells from different tissues, cells from different organs, cells from different developmental states, cells having different responses to a condition, cells having different responses to a disease, cells having different, responses to a biologically active agent, cells or tissues from different individuals, cells or tissues with different genetic modifications, and cells from different types of organisms. Exemplary eukaryotic cells from which nucleic acids can be obtained for use in a method of the invention includes, without limitation, cells from a mammal such as a rodent, mouse, rat, rabbit, guinea pig, ungulate, horse, sheep, pig, goat, cow, cat, dog, primate, human or non-human primate; a plant such as *Arabidopsis thaliana*, corn (*Zea mays*), sorghum, oat (*oryza sativa*), wheat, rice, canola, or soybean; an algae such as *Chlamydomonas reinhardtii*; a nematode such as *Caenorhabditis elegans*; an insect such as *Drosophila melanogaster*, mosquito, fruit fly, honey bee or spider; a fish such as zebrafish (*Danio rerio*); a reptile; an amphibian such as a frog or *Xenopus laevis*; a *dictyostelium discoideum*; a fungi such as *pneumocystis carinii Takifugu rubripes*, yeast, *Saccharamoyces cerevisiae* or *Schizosaccharomyces pombe*; or a *plasmodium falciparum*. Nucleic acids used in the invention can also be from a prokaryote such as a bacterium, *Escherichia coli*, staphylococci or *mycoplasma pneumoniae*; an archae; a virus such as Hepatitis C virus or human immunodeficiency virus; or a viroid. Diverse biological isolates can be obtained from two or more of these organisms. Cells from other organisms known in the art can be used as well.

Diverse biological isolates can be obtained from different cell types of one or more genomes. Exemplary cell types from which biological isolates can be obtained in a method of the invention include, without limitation, a blood cell such as a B lymphocyte, T lymphocyte, leucocyte, erythrocyte, macrophage, or neutrophil; a muscle cell such as a skeletal cell, smooth muscle cell or cardiac muscle cell; germ cell such as a sperm or egg; epithelial cell; connective tissue cell such as an adipocyte, fibroblast or osteoblast; neuron; astrocyte; stromal cell; kidney cell; pancreatic cell; liver cell; or keratinocyte. A cell used in the invention can be at a particular developmental level including, for example, a hematopoietic stem cell or a cell that arises from a hematopoietic stem cell such as a red blood cell, B lymphocyte, T lymphocyte, natural killer cell, neutrophil, basophil, eosinophil, monocyte, macrophage, or platelet. Other cells include a bone marrow stromal cell (mesenchymal stem cell) or a cell that develops therefrom such as a bone cell (osteocyte), cartilage cells (chondrocyte), fat cell (adipocyte), or other kinds of connective tissue cells such as one found in tendons; neural stem cell or a cell it gives rise to including, for example, a nerve cells (neuron), astrocyte or oligodendrocyte; epithelial stem cell or a cell that arises from an epithelial stem cell such as an absorptive cell, goblet cell, Paneth cell, or enteroendocrine cell; skin stem cell; epidermal stem cell; or follicular stem cell. Generally any type of stem cell can be used including, without limitation, an embryonic stem cell, adult stem cell, or pluripotent stem cell.

A cell from which a biological isolate is obtained for use in the invention can be a normal cell or a cell displaying one or more symptoms of a particular disease or condition. Thus, a nucleic acid used in a method of the invention can be obtained from a cancer cell, neoplastic cell, necrotic cell or the like.

Nucleic acids can be isolated from one or more cells, bodily fluids or tissues of a multicellular organism. Known methods can be used to obtain a bodily fluid such as blood, sweat, tears, lymph, urine, saliva, semen, cerebrospinal fluid, feces or amniotic fluid. Similarly known biopsy methods can be used to obtain cells or tissues such as buccal swab, mouthwash, surgical removal, biopsy aspiration or the like. Genomic DNA can also be obtained from one or more cell or tissue in primary culture, in a propagated cell line, a fixed archival sample, forensic sample or archeological sample.

Nucleic acids of a particular cell type can be prepared using methods known in the art or readily determined by those skilled in the art. Exemplary methods include those described in Sambrook et al., *Molecular Cloning: A Laboratory Manual,* 3rd edition, Cold Spring Harbor Laboratory, New York (2001) or in Ausubel et al., *Current Protocols in Molecular Biology,* John Wiley and Sons, Baltimore, Md. (1998).

A method of the invention can further include steps of isolating a particular type of cell or tissue. Exemplary methods that can be used in a method of the invention to isolate a particular cell from other cells in a population include, but are not limited to, Fluorescent Activated Cell Sorting (FACS) as described, for example, in Shapiro, Practical Flow Cytometry, 3rd edition Wiley-Liss; (1995), density gradient centrifugation, or manual separation using micromanipulation methods with microscope assistance. Exemplary cell separation devices that are useful in the invention include, without limitation, a Beckman JE-6 centrifugal elutriation system, Beckman Coulter EPICS ALTRA computer-controlled Flow Cytometer-cell sorter, Modular Flow Cytometer from Cytomation, Inc., Coulter counter and channelyzer system, density gradient apparatus, cytocentrifuge, Beckman J-6 centrifuge, EPICS V dual laser cell sorter, or EPICS PROFILE flow cytometer. A tissue or population of cells can also be removed by surgical techniques. For example, a tumor or cells from a tumor can be removed from a tissue by surgical methods, or conversely non-cancerous cells can be removed from the vicinity of a tumor. Using methods such as those set forth in further detail below, the invention can be used to compare typable loci for different cells including, for example, cancerous and non-cancerous cells isolated from the same individual or from different individuals.

In particular embodiments of the invention, a crude cell lysate containing nucleic acids can be used. Alternatively, a nucleic acid can be further isolated from other cellular components. Nucleic acids can be isolated using known methods including, for example, liquid phase extraction, precipitation, solid phase extraction, chromatography and the like. Such methods are often referred to as minipreps and are described for example in Sambrook et al., supra, (2001) or in Ausubel et al., supra, (1998) or available from various commercial vendors including, for example, Qiagen (Valencia, Calif.) or Promega (Madison, Wis.).

Nucleic acids from each of the biological isolates can be hybridized to arrays of candidate probes (18). A nucleic acid sample used in the invention can include RNA such as mRNA; DNA such as genomic DNA; or amplified products of cellular nucleic acids. An amplified product of a nucleic acid is understood to be a replicate having a substantially identical base sequence to the nucleic acid or a complement having a substantially complementary base sequence to the nucleic acid and produced by a reaction in which at least one complement is produced. Nucleic acid amplification reactions can be carried out on nucleic acids isolated from a cell. For example, cDNA can be produced by reverse transcription amplification of mRNA or genome fragments can be produced by replication of genomic DNA. Those skilled in the art will recognize that a nucleic acid produced by multiple amplification steps is an amplified product of cellular nucleic acids. For example, a cRNA produced by reverse transcription amplification of mRNA to produce cDNA followed by transcription amplification of the cDNA to produce the cRNA is an amplified product of the mRNA (and the cDNA). Accordingly, an amplified product of a nucleic acid from a cell is considered to be from the cell. A nucleic acid used in the invention can be single or double stranded.

After hybridization, the arrays can be scanned and hybridization intensity pattern data generated for each probe (20). Intensity of hybridization can be detected due to the presence of a label in the hybrid or due to modification of a member of the hybrid to include a label. In cases where a member of a hybrid is modified, the hybrid can be dissociated, if desired and detection of the labeled member subsequently carried out. A label useful in the invention can be a primary label that is directly detectable or secondary label that can be indirectly detected, for example, via direct or indirect interaction with a primary label. Exemplary primary labels include, without limitation, an isotopic-label such as a naturally non-abundant radioactive or heavy isotope; chromophore; luminophore; fluorophore; calorimetric agent; magnetic substance; electron-rich material such as a metal; electrochemiluminescent label such as $Ru(bpy)_3^{2+}$; or moiety that can be detected based on a nuclear magnetic, paramagnetic, electrical, charge to mass, or thermal characteristic. Fluorophores that are useful in the invention include, for example, fluorescent lanthanide complexes, including those of Europium and Terbium, fluorescein, rhodamine, tetramethylrhodamine, eosin, erythrosin, coumarin, methyl-coumarins, pyrene, Malacite green, Cy3, Cy5, stilbene, Lucifer Yellow, Cascade Blue™, Texas Red, alexa dyes, phycoerythin, bodipy, and others known in the art such as those described in Haugland, *Molecular Probes Handbook*, (Eugene, Oreg.) 6th Edition; The Synthegen catalog (Houston, Tex.), Lakowicz, *Principles of Fluorescence Spectroscopy*, 2nd Ed., Plenum Press New York (1999), or WO 98/59066. Labels can also include enzymes such as horseradish peroxidase or alkaline phosphatase or particles such as magnetic particles or optically encoded nanoparticles.

Exemplary secondary labels are binding moieties. A binding moiety can be attached to a nucleic acid to allow detection or isolation of the nucleic acid via specific affinity for a receptor or other binding moiety. Exemplary pairs of binding moieties that can be used in the invention include, without limitation, antigen and immunoglobulin or active fragments thereof, such as FAbs; immunoglobulin and immunoglobulin (or active fragments, respectively); avidin and biotin, or analogs thereof having specificity for avidin such as imino-biotin; streptavidin and biotin, or analogs thereof having specificity for streptavidin such as imino-biotin; carbohydrates and lectins; and other known proteins and their ligands. It will be understood that either partner in the above-described pairs can be attached to a nucleic acid and detected or isolated based on binding to the respective partner. It will be further understood that several moieties that can be attached to a nucleic acid can function as both primary and secondary labels in a method of the invention. For example, streptavidin-phycoerythrin can be detected as a primary label due to fluorescence from the phycoerythrin moiety or it can be detected as a secondary label due to its affinity for anti-streptavidin antibodies, as set forth in further detail below in regard to signal amplification methods.

In a particular embodiment, the secondary label can be a chemically modifiable moiety. In this embodiment, labels having reactive functional groups can be incorporated into a nucleic acid. The functional group can be subsequently covalently reacted with a primary label. Suitable functional groups include, but are not limited to, amino groups, carboxy groups, maleimide groups, oxo groups and thiol groups. Binding moieties can be particularly useful when attached to primers used for amplification of a gDNA because an amplified representative population of genome fragments produced with such primers can be attached to an array via said binding moieties. Furthermore, binding moieties can be useful for separating amplified fragments from other components of an amplification reaction, concentrating the amplified representative population of genome fragments, or detecting one or more members of an amplified representative population of genome fragments when bound to capture probes on an array. Exemplary separation and detection methods for nucleic acids having attached binding moieties are set forth below in further detail.

The above-described labels can be detected using methods well known in the art including, for example, those typically used for detection of probe arrays as described in the references disclosed below in regard to various array types. Analysis of the intensity pattern data can then be performed to select one or more probes from among the set of candidate probes (22).

As used herein, the term "array" refers to a population of different probe molecules that are attached to one or more substrates such that the different probe molecules can be differentiated from each other according to relative location. An array can include different probe molecules that are each located at a different addressable location on a substrate. Alternatively, an array can include separate substrates each bearing a different probe molecule, wherein the different probe molecules can be identified according to the locations of the substrates on a surface to which the substrates are associated or according to the locations of the substrates in a liquid. Arrays useful in the invention are described, for example, in U.S. Pat. Nos. 6,023,540, 6,200,737, 6,327,410, 6,355,431 and 6,429,027; US patent application publication No. US 2002/0102578 and PCT Publication Nos. WO 00/63437, WO 98/40726, and WO 98/50782.

An exemplary array that can be used is an array of arrays or a composite array having a plurality of individual arrays that is configured to allow processing of multiple samples. Such arrays allow multiplex detection of large pluralities of target loci and/or interrogation of large populations of probes. Exemplary composite arrays that can be used in the invention are described in U.S. Pat. No. 6,429,027 and U.S. Pat. App. Pub. No. 2002/0102578. In particular embodiments, each individual array can be present within each well of a microtiter plate by attachment to the well or temporary introduction to the well.

Further examples of microarrays that can be used in the invention include, without limitation, those described in U.S. Pat. Nos. 6,287,768; 6,288,220; 6,287,776; 6,297,006 and 6,291,193 U.S. Pat. Nos. 5,429,807; 5,436,327; 5,561,071; 5,583,211; 5,658,734; 5,837,858; 5,874,219; 5,919,523; 6,136,269; 6,287,768; 6,287,776; 6,288,220; 6,297,006; 6,291,193; 6,346,413; 6,416,949; 6,482,591; 6,514,751 and 6,610,482; and WO 93/17126; WO 95/11995; WO 95/35505; EP 742 287; and EP 799 897. Further examples of array formats that are useful in the invention are described in U.S. Pat. No. 6,355,431 B1, US 2002/0102578 and PCT Publication No. WO 00/63437. Exemplary formats that can be used in the invention to distinguish beads in a fluid sample using microfluidic devices are described, for example, in U.S. Pat. No. 6,524,793. Commercially available fluid formats for distinguishing beads include, for example, those used in xMAP™ technologies from Luminex or MPSS™ methods from Lynx Therapeutics.

Arrays used in the invention can be made by various techniques and technologies. For example, Affymetrix® GeneChip® arrays can be synthesized in accordance with techniques sometimes referred to as VLSIPS™ (Very Large Scale Immobilized Polymer Synthesis) technologies. A spotted array can also be used in a method of the invention. An exemplary spotted array is a CodeLink™ Array available from Amersham Biosciences. An array that is useful in the invention can also be manufactured using inkjet printing methods such as SurePrint™ Technology available from Agilent Technologies.

Figure 2:
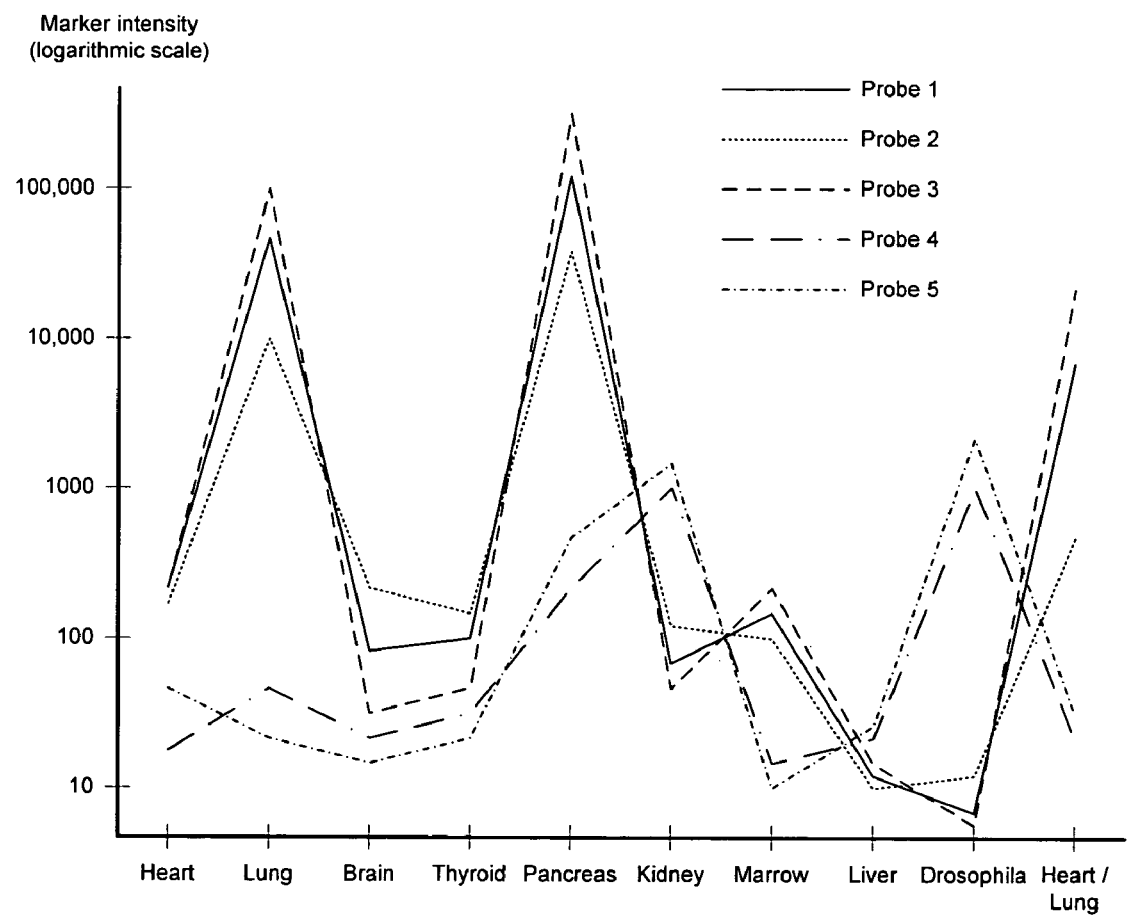
FIG. 2 shows a graphical representation of intensity pattern data for a hypothetical set of candidate probes.

FIG. 2 shows a graphical representation of intensity pattern data for a hypothetical set of five candidate probes hybridized to mRNA from a panel of ten diverse cell types. This graph will be referred to in the following discussions of particular embodiments to illustrate the application of various probe selection principles.

Several embodiments of the invention are now described. In general terms, these embodiments relate to probe selection techniques applied to empirical data representing candidate probe intensities across a panel of diverse biological isolates, and to the biological isolates selected for hybridization to candidate probes and selection techniques related to particular biological isolates.

First Embodiment

In accordance with a first embodiment of the invention, probes are selected from among the candidate probes based on similarities among their differential responses to target nucleic acids from the various biological isolates to which the probes are hybridized. For purposes of this disclosure, the term differential response refers to the relative difference in the amount of hybridization that occurs between a candidate probe and different target nucleic acids such as target nucleic acids from different biological isolates. This differential response is typically indicated by the intensity data for each candidate probe. This embodiment applies the principle that the most selective probes among a set of candidate probes will have the most similar differential responses across a set of diverse biological isolates. This principle may be illustrated through reference to the intensity patterns of FIG. 2. In that figure, probes 1, 2 and 3 can be seen to have very similar patterns, while probes 4 and 5 are similar to each other and rather different from probes 1, 2 and 3. In accordance with the principle applied in the first embodiment, probes 1, 2 and 3 are expected to have selectivity to the most common form of the target sequence because they exhibit highly similar behavior across a panel of diverse biological isolates.

Figure 3:
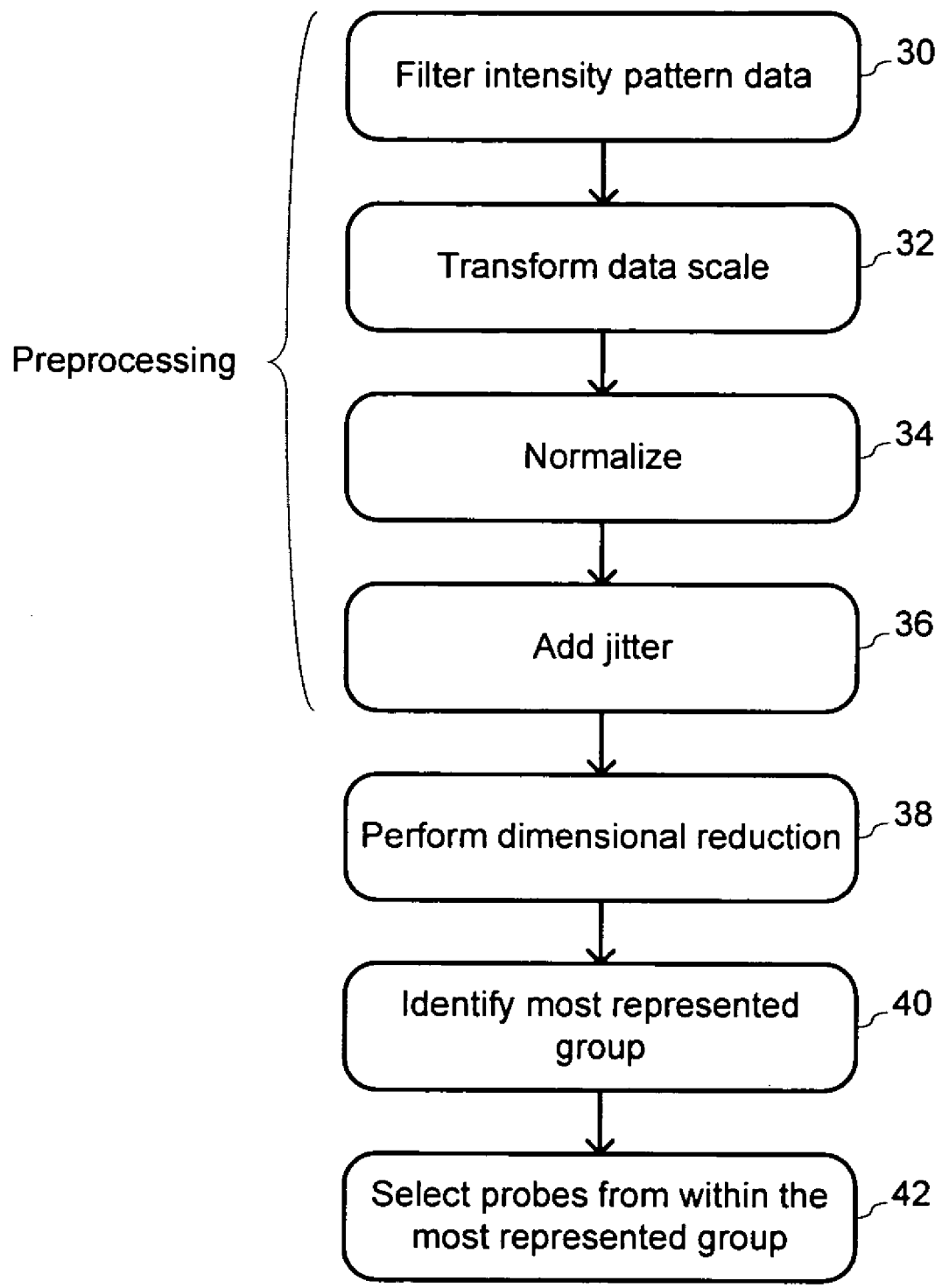
FIG. 3 shows a process flow in accordance with one implementation of a first embodiment of the invention.

A process flow for one implementation of the first embodiment is shown in FIG. 3. In general terms, this implementation assesses similarities among the differential responses of candidate probes by treating each intensity pattern as an N-dimensional value, where each biological isolate is a dimension and the intensity value for the biological isolate is the value of the pattern in that dimension. A dimensional reduction process is performed, whereby each N-dimensional pattern is represented by a 1-dimensional value, such that the difference between any two 1-dimensional values is representative of the relative similarities of their respective patterns.

As seen in FIG. 3, the process flow of this implementation includes several sub-processes that are referred to collectively as preprocessing. The preprocessing includes a filtering process (30) whereby intensity patterns for certain candidate probes are eliminated from further consideration based on various filtering criteria. Filtering can be carried out to remove probes that do not have a strong differential response when hybridized to nucleic acids from different cells. Examples of filtering criteria include: eliminating probes having no intensity values exceeding a given threshold; eliminating probes having a median intensity value that does not exceed a given threshold; eliminating probes that do not have an intensity value for a given number of biological isolates or for any biological isolates; eliminating probes that have a coefficient of variation (i.e., normalized standard deviation) that is less than a given value; and, eliminating probes having low entropy. Entropy is a measure of the variability of the signal across different tissues. Signals with low variability, i.e., low entropy, can be filtered out. These filtering criteria and other filtering criteria may be used together or in various other combinations. For example, filtering criteria may be used individually to eliminate candidate probes, or may be used to generate a score for each filtering criterion, with candidate probes being eliminated based on their cumulative scores for all filtering criteria.

After filtering, additional processing can be performed to transform the scale of the intensity pattern data (32). For example, the intensity values may be converted to logarithmic values to compress their scale. This provides the advantage of giving equivalent weight to equivalent relative changes even when such changes occur at different magnitudes of intensity. Alternatively, a square root function or BoxCox transformation may be used. After scale transformation, the intensity pattern data can be normalized (34). This may be performed in any of a variety of manners, such as by dividing the intensity values of each pattern by the median value of the pattern. After normalization, "jitter" can be added to the intensity pattern data (36), for example, in the form of random intensity patterns that provide a uniform distribution of intensity values between the minimum and maximum values of the actual intensity patterns. The addition of jitter can be used to improve the identification of the boundaries of probe activities represented in reduced space, for example, in step 38 as set forth below.

While the preprocessing described above is preferred for the implementation described here, it will be appreciated that these preprocessing tasks and other preprocessing tasks may be used alone or in various other combinations and temporal orders.

After preprocessing is completed, a dimensional reduction process can be performed on the pattern data, including the random jitter patterns as well as the set of actual candidate probe patterns. In the present implementation, the dimensional reduction process is performed by providing the intensity patterns as inputs to a NeuroScale neural network. The NeuroScale neural network utilizes a radial basis function such as a thin plate spline (TPS) to perform a dimension-reducing topographic transformation of data that optimally preserves the geometric structure of the data while reducing it from an N-dimensional data space to a 1-dimensional feature space. In effect, the NeuroScale neural network receives the intensity pattern data and generates a number corresponding to each pattern, with the pairwise similarities of any two patterns corresponding to the pairwise similarities of the original patterns. As a result, highly similar patterns are assigned very similar numbers, while highly dissimilar patterns are assigned very different numbers. For example, referring to the hypothetical patterns of FIG. 2, probes 1, 2 and 3 of that figure would be assigned similar numbers, while probes 4 and 5 would also be assigned numbers that are similar yet significantly different from the numbers assigned to probes 1-3.

More information concerning the NeuroScale neural network is provided in the paper by David Lowe and Michael E. Tipping of the Neural Computing Research Group, Aston University, Birmingham UK, entitled "NeuroScale: Novel Topographic Feature Extraction using RBF Networks," which is published in Advances in Neural Information Processing Systems, Vol. 9, Proceedings of the 1996 Conference, the entirety of which is incorporated herein by reference for its teachings concerning the NeuroScale neural network.

NeuroScale itself requires a training step and a feedforward pass through the trained network.

The 1-dimensional data produced by the NeuroScale neural network can be used to identify a most-represented group among the probes (40). The most represented group can be identified by computing a probability density estimate such as a histogram for the 1-dimensional data. In particular implementations, the data range of the set of 1-dimensional values is divided into a set of equally sized bins, and each bin is examined to determine how many values for actual probes fall within it. Among these bins, the bin containing the most actual probe values is identified. If necessary, for example, in the event of a tie, the histogram may be adjusted by changing the bin size or changing the minimum and maximum values of the data range until a maximum bin is identified. Other probability density estimation methods are also known in the art and can be used as well for identifying the most represented group, and their parameters may be adjusted as needed to identify a most-represented group.

The most-represented group of 1-dimensional values will include the largest set of actual intensity patterns having the greatest similarity among all intensity patterns. In accordance with the similarity principle described above, this similarity is taken to indicate that the corresponding probes exhibit the greatest selectivity with respect to the target nucleic acid sequence among the candidate probes.

Further processing may then be performed to select a subset of the most-represented probes (42). For example, a subset of probes may be selected based on the similarity of their 1-dimensional values. In one implementation, the two probes within the most-represented set having the closest values are selected. Alternative selection criteria may also be implemented. For example, a different predefined number of candidate probes may be selected based on their similarities as represented by their 1-dimensional values. The candidate probes of the most-represented group may also be used as an initial set of candidate probes for further selection techniques as described below, for example, in regard to the fifth embodiment.

Second Embodiment

In accordance with a second embodiment of the invention, the nucleic acids from diverse biological isolates to which candidate probes are hybridized may include mixtures in known ratios of multiple diverse biological isolates. The ratio can be determined based on the amount of cells, tissue or organs from which each isolate is derived. The cell types used in the mixture can include those having nucleic acids to which the candidate probes can hybridize individually. This embodiment applies the principle that a desirable probe will have a pattern of hybridization to a mixture of nucleic acids from several diverse biological isolates that is predictable from its patterns of hybridization to the nucleic acids from each of the biological isolates individually.

Figure 4:
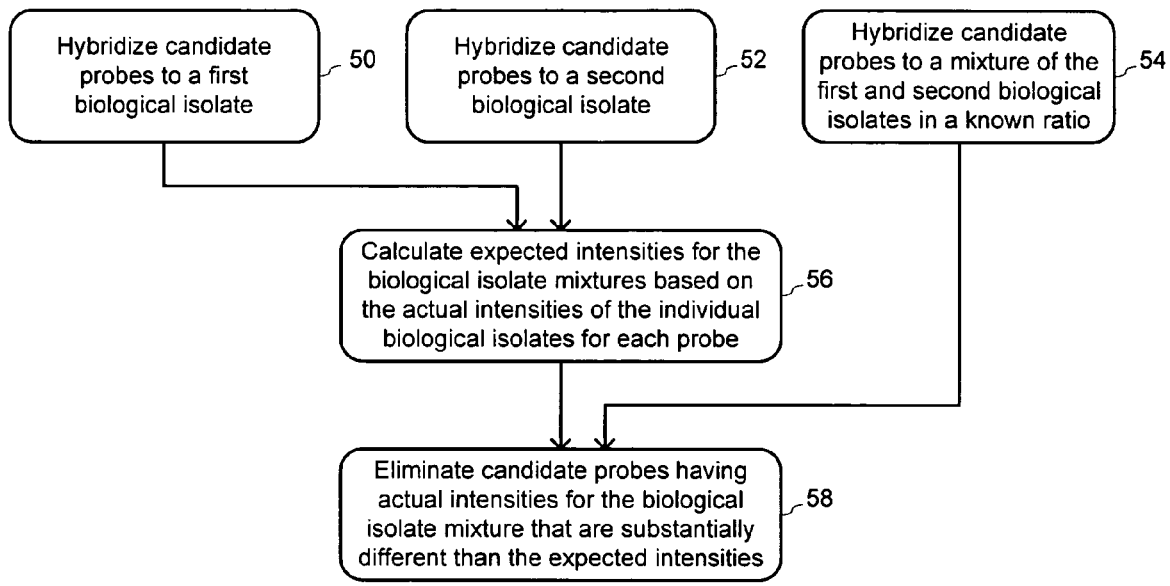
FIG. 4 shows a process flow in accordance with one implementation of a second embodiment of the invention.

A process flow for an implementation of this embodiment is shown in FIG. 4. Candidate probes are hybridized to nucleic acids from a first biological isolate (50) and to those from a second biological isolate that is different from the first biological isolate (52). For example, candidate probes may be hybridized to nucleic acids from, among others, heart cells and lung cells. In accordance with the second embodiment, the candidate probes can also be hybridized to one or more samples comprised of a mixture in a known ratio of nucleic acids from biological isolates to which the probes are also hybridized individually (54). For example, the probes may be hybridized to a 1:1 mixture of nucleic acids from heart cells and lung cells. Based on the intensity values exhibited by the candidate probes upon hybridization to the first and second biological isolates individually, an expected intensity value for the heart/lung mixture is calculated for each probe (56). For example, if a probe exhibits a signal intensity of 10,000 for heart cells and a signal intensity of 300 for lung cells, its expected signal intensity in the presence of a 1:1 mixture of heart and lung cells is (0.5)(10,000)+(0.5)(300)=5150. Once the expected values have been calculated for each candidate probe, those candidate probes having actual values for the mixture that are substantially different from their expected values can be eliminated (58). Significant deviation from the expected value indicates that the candidate probe is undesirable and the candidate probe can be eliminated on that basis. The amount of deviation required to eliminate a candidate probe from further consideration may be established in accordance with the particular implementation. Depending upon the particular application of the methods, deviation that indicates that a probe should be eliminated can be for example, at least about 25%, 50%, 100%, 2 fold, 5 fold or 10 fold.

The principle applied by this embodiment is illustrated in the graph of FIG. 2. In FIG. 2, probe 2 is seen to have a value of approximately 100 for heart cells and a value of approximately 10,000 for lung cells. The expected value for a mixture of these cells is approximately 5,000, however as seen in the graph, the actual value is less than 1000. Probe 2 may be eliminated from further consideration on the basis of this 5 fold deviation.

Further implementations in accordance with this embodiment may utilize multiple mixture samples, including mixtures of different biological isolates, the same biological isolates in different ratios, or a single biological isolate with a neutral medium in different concentrations. Implementations in accordance with this embodiment may also be combined with other embodiments as discussed below, for example, in regard to the fifth embodiment.

Third Embodiment

In accordance with a third embodiment of the invention, the diverse biological isolates to which candidate probes are hybridized may be derived from one or more types of cells, tissues or organs from an organism having a genome that is essentially orthogonal to the genome of the organism of interest. For purposes of this disclosure, a genome is considered to be essentially orthogonal to the genome of an organism of interest if that genome has few to no genes in common with the organism of interest. Typically, orthogonal genomes contain adequate sequence divergence such that under a particular set of stringent hybridization assay conditions sequences from the genome of interest would not be expected to specifically hybridize to the orthogonal genome. Accordingly, orthogonal genomes useful in the methods can have, for example, less than about 50%, 40%, 30%, 20%, 10% or 5% genome sequence homology. This embodiment applies the principle that a desirable probe will exhibit relatively little hybridization to nucleic acid sequences that are known to be unlike those of the target sequence.

Figure 5:
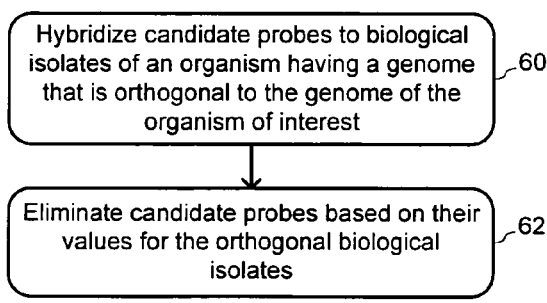
FIG. 5 shows a process flow in accordance with one implementation of a third embodiment of the invention.

A process flow for an implementation of this embodiment is shown in FIG. 5. Candidate probes are hybridized to nucleic acids from an organism having a genome that is essentially orthogonal to the genome of the organism of interest (60). For example, when evaluating candidate probes for a nucleic acid sequence of the human genome, the candidate probes may be hybridized to one or more biological isolates from organisms of the genus *Drosophila* (such as *Drosophila melanogaster*, commonly known as the fruit fly).

After hybridization to the orthogonal biological isolates, candidate probes are eliminated based on the intensity values exhibited for hybridization to the orthogonal biological isolates (62). For example, a threshold intensity value may be set for the *Drosophila* sample, with any probes that exceed that value being eliminated from further consideration. The application of this principle is illustrated with reference to the intensity patterns of FIG. 2. In that figure, probes 4 and 5 are seen to have intensity values that exceed 100 for the *Drosophila* cell sample, while the remaining probes have very low values for *Drosophila*. Assuming a threshold intensity value of, for example, 50, probes 4 and 5 will be eliminated from further consideration while the other probes are retained.

Further implementations in accordance with this embodiment may utilize multiple cell types from one or more orthogonal organisms. Implementations in accordance with this embodiment may also be combined with other embodiments as discussed below, for example, in regard to the fifth embodiment.

Fourth Embodiment

In accordance with a fourth embodiment of the invention, probes are selected from among the candidate probes based on their dynamic response, in other words, based on the amount of variation of their hybridization intensity values across diverse biological isolates. This embodiment applies the principle that the most selective probes among a set a candidate probes will exhibit the greatest variation of intensities, also referred to herein as entropy, across a set of diverse biological isolates.

Figure 6:
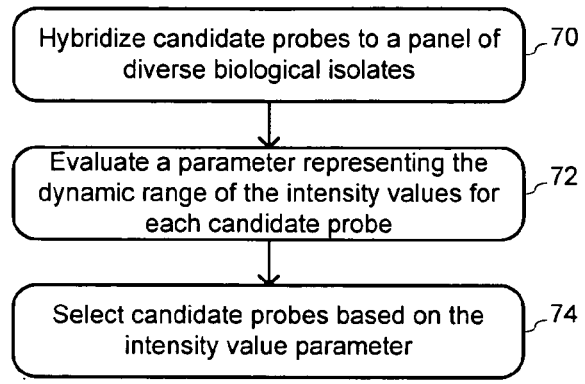
FIG. 6 shows a process flow in accordance with one implementation of a fourth embodiment of the invention.

A process flow for an implementation of this embodiment is shown in FIG. 6. In accordance with this implementation, a set of candidate probes is hybridized to nucleic acids from a panel of diverse biological isolates (70). For each candidate probe, a parameter representing the dynamic response of the probe is then evaluated (72). Examples of parameters representing the dynamic response of a candidate probe include: the difference between the greatest intensity value for the probe and the least intensity value for the probe; the difference between intensities of a first quantile of the intensity pattern data and intensities in a second quantile of the intensity pattern data; the division of the greatest intensity value for the probe by the least intensity value for the probe; the log of the ratio of the greatest intensity and the least intensity of the intensity pattern; the arctangent of the log of the ratio of the greatest intensity and the least intensity of the intensity pattern; the standard deviation of the intensity values for the probe; and, the coefficient of variation of the intensity values of the probe. Preprocessing as described in connection with the first embodiment may be performed on the pattern data prior to evaluation of these parameters. One or more candidate probes can then be selected based on this parameter (74).

This implementation is further illustrated with reference to the intensity patterns of FIG. 2. As seen in that figure, the pattern for probe 3 exhibits both the highest intensity value (pancreas) and the lowest intensity value (*Drosophila*) among all of the candidate probes. This probe will tend to yield the greatest value for any parameter representing dynamic response and will therefore be selected from among the five candidate probes.

This embodiment may be used to select a single probe, a predetermined number of probes having the greatest dynamic response among all candidate probes, or an arbitrary number of probes having dynamic responses that exceed a threshold value.

While the processing of this embodiment generally provides good probe selection, it is possible that the greatest dynamic response will be exhibited by one or more candidate probes that target a splice isoform whose expression levels vary to a greater degree than the expression levels of the most accurate candidate probes. This may be avoided by combining the techniques of this embodiment with the techniques of other embodiments, as described herein.

Fifth Embodiment

In accordance with a fifth embodiment of the invention, probes are selected from among the candidate probes by evaluating several parameters of the intensity pattern data for each candidate probe, and then combining the parameters using a predetermined weighting formula. Probes are then selected based on the combined weighted scores for each candidate probe. This embodiment allows the application of multiple principles of probe selection in various combinations.

Figure 7:
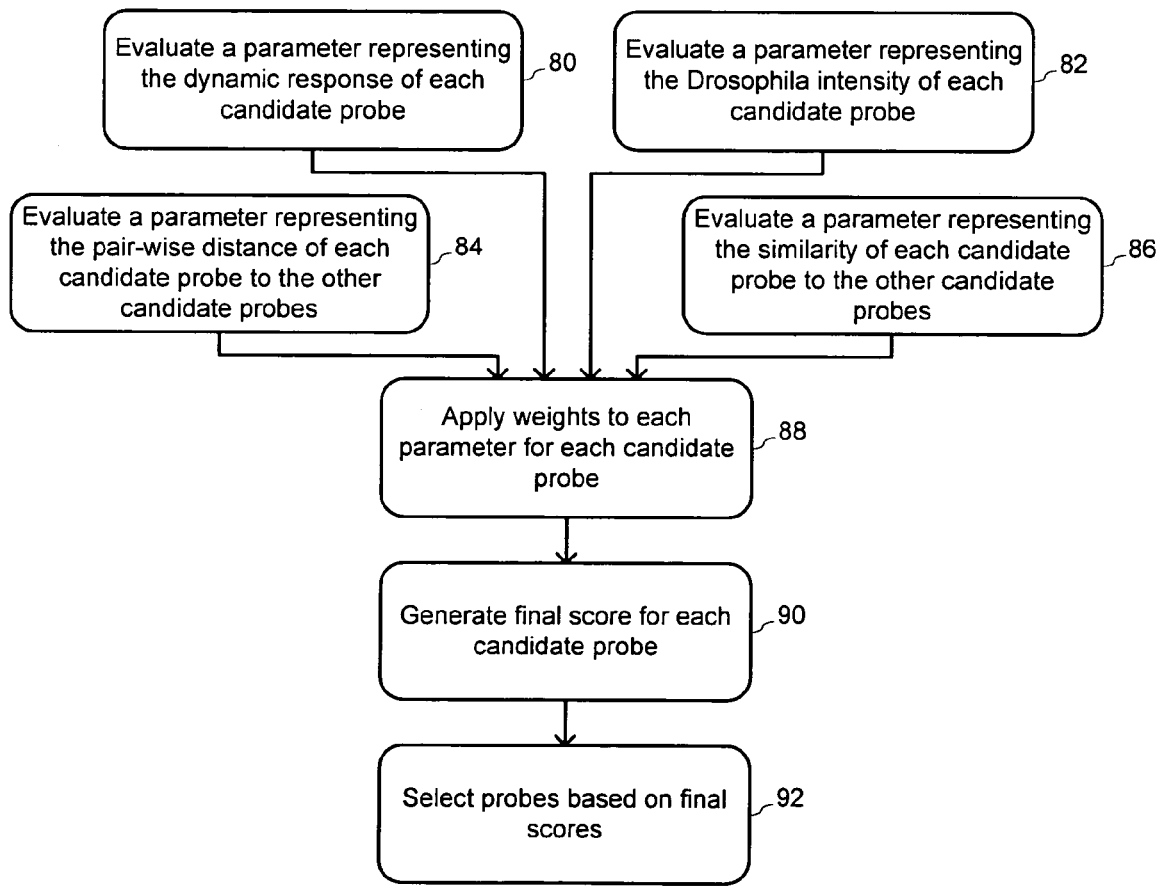
FIG. 7 shows a process flow in accordance with one implementation of a fifth embodiment of the invention.

A process flow for one implementation in accordance with the fifth embodiment is shown in FIG. 7. In this implementation, four parameters are evaluated for each candidate probe. One of the parameters that is evaluated is the dynamic response of each candidate probe (80). The dynamic response in this implementation is represented by the standard deviation of the log 10 transformed intensity values of the candidate probe. A bias may be added to the intensity values of each candidate probe before calculating the logarithm. The logarithm curve typically has a very high slope for small values. This can result in exaggeration of small values after the logarithmic transformation. By adding bias, this effect can be ameliorated.

Another parameter that can be evaluated for each candidate probe is the intensity of the probe when hybridized to *Drosophila* nucleic acids (82). This score may be evaluated as a simple binary score of 1 or 0 indicating whether the intensity for *Drosophila* exceeded a predetermined threshold value.

Another parameter that can be evaluated is the pair-wise distance of each candidate probe to the other candidate probes (84). This parameter may be evaluated by normalizing the intensity patterns, transforming the scale of the intensity patterns, and then, for each candidate probe, summing the absolute differences between the hybridization intensity values of the candidate probe and each other candidate probe for nucleic acids of each biological isolate to yield a final sum for each candidate probe. Alternatively, the squared distances may be summed, and then the square root of the sum may be calculated.

Another parameter that can be evaluated for each candidate probe is the similarity of the hybridization intensity pattern of the candidate probe to the hybridization intensity patterns of other candidate probes (86). This parameter may be evaluated by first calculating, for each possible pair of candidate probes, a value indicating the degree to which the hybridization intensity values of the pair change in the same direction from biological isolate to biological isolate. For example, each change in the same direction may be assigned a score of one, and each change in the opposite direction may be assigned a score of negative one. These scores can be assigned for each change of biological isolate and then summed to yield a final score for the pair of candidate probes. After a score is generated for each pair of candidate probes, a score is generated for each individual candidate probe by summing the scores for each pair that includes that candidate probe.

After evaluating these parameters, weights can be applied to the parameters evaluated for each candidate probe (88). In the present implementation, the weights are selected such that the dynamic response parameter is heavily weighted, the *Drosophila* parameter is moderately weighted, and the pair-wise distance and similarity parameters are lightly weighted. These weights reflect a judgment as to the relative significance of each parameter in indicating the over-all desirability of a candidate probe. The weights may be predefined or may be configurable by the user.

After applying weights to each parameter, the weighted parameters are summed to generate a final score for each candidate probe (90), and candidate probes are selected based on their final scores (92). The score may be used to select a single probe, a predetermined number of probes having the greatest scores among all candidate probes, or an arbitrary number of probes having scores that exceed a threshold value.

This embodiment is not limited to the use of the parameters of the illustrated embodiment, but rather other types and numbers of parameters may be evaluated and weighted in order to apply a desired combination of probe selection principles to the set of candidate probes. For example, it may be evaluated whether the hybridization intensity pattern for the candidate probe includes a hybridization intensity value for each of the diverse types biological isolates.

Sixth Embodiment

The processes of the second through fifth embodiments may be implemented to select probes from among a set of candidate probes identified through informatic methods. However, in some instances it may be desirable to refine the set of candidate probes prior to application of these embodiments. In accordance with a sixth embodiment, the dimensional reduction process of the first embodiment is used to identify one or more most-represented groups of candidate probes. Processing of any of the second through fifth embodiments is then performed on the sets of candidate probes of each of the most represented groups to select the best probes from among those groups.

For example, referring to the intensity patterns of FIG. 2, processing using dimensional reduction may be applied to identify probes 1, 2 and 3 as a set of candidate probes having highly similar patterns. Candidate probes may then be selected from or eliminated from this subset based on various parameters such as dynamic response, *Drosophila* intensity, heart/lung mixture intensity, pair-wise distance, pattern similarity, or a weighted combination of these or other parameters.

The devices, features and processing described herein are not exclusive of other devices, features and processing, and variations and additions may be implemented in accordance with the particular objectives to be achieved. For example, a system performing processing as described above may be integrated with other systems not described herein to provide further combinations of features, to operate concurrently on the same computing devices, or to serve other types of users. Further, in some instances the processing steps recited herein need not be implemented on a computing device, but may be performed in an alternate manner. Thus, while the embodiments illustrated in the figures and described above are presently preferred for various reasons as described herein, it should be understood that these embodiments are offered by way of example only. The invention is not limited to a particular embodiment, but extends to various modifications, combinations, and permutations encompassed by the claims and their equivalents.

Throughout this application various publications, patents and patent applications have been referenced. The disclosure of these publications, patents and patent applications in their entireties are hereby incorporated by reference in this application in order to more fully describe the state of the art to which this invention pertains.

The term "comprising" is intended herein to be open-ended, including not only the recited elements, but further encompassing any additional elements.

What is claimed is:

1. A method for selecting nucleic acid probes based on similarities among differential responses in hybridizing to target nucleic acid sequences, comprising:
   (a) selecting a set of candidate probes;
   (b) hybridizing said candidate probes to nucleic acid sequences of each of a set of target nucleic acid sequences representing diverse biological isolates;
   (c) processing intensity pattern data for said set of candidate probes, wherein the intensity pattern data represents intensities of markers associated with said candidate probes upon hybridization to said nucleic acid sequences of each of said set of target nucleic acid sequences representing diverse biological isolates, and wherein said processing generates a one-dimensional value corresponding to each candidate probe, and wherein the relative similarities between said one-dimensional values represent the relative similarities of their differential responses;
   (d) identifying a most represented group among said one-dimensional values; and
   (e) selecting nucleic acid probes from candidate probes corresponding to said most represented one-dimensional values;
   wherein said processing is performed by a NeuroScale neural network.

2. A method for selecting nucleic acid probes based on similarities among differential responses in hybridizing to target nucleic acid sequences, comprising:
   (a) selecting a set of candidate probes;
   (b) hybridizing said candidate probes to nucleic acid sequences of each of a set of target nucleic acid sequences representing diverse biological isolates;
   (c) processing intensity pattern data for said set of candidate probes, wherein the intensity pattern data represents intensities of markers associated with said candidate probes upon hybridization to said nucleic acid sequences of each of said set of target nucleic acid sequences representing diverse biological isolates, and wherein said processing generates a one-dimensional value corresponding to each candidate probe, and wherein the relative similarities between said one-dimensional values represent the relative similarities of their differential responses;
   (d) identifying a most represented group among said one-dimensional values; and
   (e) selecting nucleic acid probes from candidate probes corresponding to said most represented one-dimensional values;
   wherein identifying a most represented group of said one-dimensional values comprises generating a probability density estimate of said one-dimensional values; and
   wherein at least one of the following applies: (a) said probability density estimate comprises a histogram, and identifying a most represented group of said one-dimensional values comprises identifying a maximum bin of said histogram; (b) generating said probability density estimate comprises adjusting bins to produce said maximum bin; or (c) generating said probability density estimate comprises adjusting the parameters of a density estimator.

3. The method of claim 2, wherein said probability density estimate comprises a histogram, and wherein identifying a most represented group of said one-dimensional values comprises identifying a maximum bin of said histogram.

4. The method of claim 2, wherein said generating said probability density estimate comprises adjusting bins to produce said maximum bin.

5. The method of claim 4, wherein adjusting said bins comprises changing the number of bins.

6. The method of claim 4, wherein adjusting said bins comprises adjusting one or more of a maximum and a minimum value of the data range.

7. The method of claim 4, wherein adjusting said bins comprises changing the number of bins and adjusting one or more of a maximum and a minimum value of the data range.

8. The method of claim 2, wherein generating said probability density estimate comprises adjusting the parameters of a density estimator.

9. A method for selecting nucleic acid probes based on similarities among differential responses in hybridizing to target nucleic acid sequences, comprising:
   (a) selecting a set of candidate probes;
   (b) hybridizing said candidate probes to nucleic acid sequences of each of a set of target nucleic acid sequences representing diverse biological isolates;
   (c) processing intensity pattern data for said set of candidate probes, wherein the intensity pattern data represents intensities of markers associated with said candidate probes upon hybridization to said nucleic acid sequences of each of said set of target nucleic acid sequences representing diverse biological isolates, and wherein said processing generates a one-dimensional value corresponding to each candidate probe, and wherein the relative similarities between said one-dimensional values represent the relative similarities of their differential responses;
   (d) identifying a most represented group among said one-dimensional values; and
   (e) selecting nucleic acid probes from candidate probes corresponding to said most represented one-dimensional values;
   wherein identifying said most represented group comprises designating a predefined number of candidate probes having the least differences among the one-dimensional values of said probes of said most represented group as represented by said one-dimensional values.

10. The method of any one of claims 1, 2 or 9, wherein said biological isolates are derived from cells from different tissues.

11. The method of any one of claims 1, 2 or 9, wherein said biological isolates are derived from cells from different organs.

12. The method of any one of claims 1, 2 or 9, wherein said biological isolates are derived from cells from different developmental states.

13. The method of any one of claims 1, 2 or 9, wherein said biological isolates are derived from cells having different responses to a condition of the organism of interest.

14. The method of any one of claims 1, 2 or 9, wherein said biological isolates are derived from cells having different responses to a disease of the organism of interest.

15. The method of any one of claims 1, 2 or 9, wherein said biological isolates are derived from cells having different responses to a biologically active agent.

16. The method of any one of claims 1, 2 or 9, further comprising excluding at least one candidate probe outside of said most represented group from a set of said selected probes.

17. The method of any one of claims 1, 2 or 9, wherein preprocessing is performed on said intensity pattern data before said processing.

18. The method of claim 17, wherein preprocessing comprises filtering said intensity pattern data to eliminate probes from said candidate set.

19. The method of claim 18, wherein said filtering comprises eliminating probes based on entropy of their intensity patterns.

20. The method of claim 18, wherein said filtering comprises eliminating any probe having a maximum intensity that does not exceed a predefined threshold.

21. The method of claim 18, wherein said filtering comprises eliminating any probe having a median intensity that does not exceed a predefined threshold.

22. The method of claim 18, wherein said filtering comprises eliminating any probe that is lacking an intensity value for all of said diverse biological isolates.

23. The method of claim 18, wherein said filtering comprises eliminating any probe having a coefficient of variation that is less than a predetermined threshold.

24. The method of claim 17, wherein said preprocessing comprises transforming the intensity pattern data into log values of the intensities corresponding to each biological isolate.

25. The method of claim 17, wherein said preprocessing comprises normalizing the intensity pattern for each probe.

26. The method of claim 25, wherein said normalizing is performed by dividing the intensity values of each intensity pattern by the median intensity value of that intensity pattern.

27. The method of claim 17, wherein said preprocessing comprises adding random intensity pattern data to the set of intensity pattern data for said candidate probes.

28. The method of any one of claims 2, 4 or 9, wherein said processing is performed by a NeuroScale neural network.

29. The method of any one of claims 16, wherein said processing is performed by a NeuroScale neural network.

30. The method of any one of claims 18, wherein said processing is performed by a NeuroScale neural network.

31. The method of any one of claims 25, wherein said processing is performed by a NeuroScale neural network.

32. The method of any one of claims 27, wherein said processing is performed by a NeuroScale neural network.

* * * * *